United States Patent [19]

Detre et al.

[11] Patent Number: 4,943,307
[45] Date of Patent: Jul. 24, 1990

[54] PLANT-PROTECTIVE PESTICIDAL COMPOSITION

[75] Inventors: Tamaás Detre, Nagymaros; Sándor Ángyán, Budapest; László Pap, Budapest; András Szegő, Budapest; Zoltán Karádi, Budapest; Klára Bertus née Bende, Sződliget; Katalin Mármarosi née Kellner, Biatorbágy, all of Hungary

[73] Assignee: Chinoin Gyogyszer Es Vegyeszeti Termekek Gyara Rt., Budapest, Hungary

[21] Appl. No.: 220,018

[22] Filed: Jul. 15, 1988

[30] Foreign Application Priority Data

Jul. 16, 1987 [HU] Hungary ............... 22513245/87

[51] Int. Cl.$^5$ .................. A01N 25/02; A01N 43/00; C07C 65/12; C07C 211/30

[52] U.S. Cl. .................. 71/3; 514/471; 514/478; 514/481; 514/484; 514/486; 514/588; 514/596; 514/597; 514/598; 514/609; 514/613; 514/625; 514/626; 514/628; 514/646; 514/918; 514/936; 514/937; 514/942; 514/950; 514/970; 514/973; 514/75; 514/80; 514/86; 514/87; 514/89; 514/120; 514/183; 514/242; 514/255; 514/361; 514/362; 514/373; 514/378; 514/383; 514/384; 514/398; 514/400; 514/467; 514/468; 514/470; 71/11; 71/86; 71/87; 71/111; 71/118; 71/119; 71/125; 71/DIG. 1

[58] Field of Search .............. 514/361, 362, 373, 588, 514/596, 597, 598, 609, 613, 625, 626, 628, 646, 183, 242, 255, 378, 383, 384, 398, 399, 400, 918, 936, 937, 942, 950, 970, 973, 978

[56] References Cited

U.S. PATENT DOCUMENTS

| | | | |
|---|---|---|---|
| 4,405,353 | 9/1983 | Angyan et al. | 71/DIG. 1 |
| 4,452,630 | 6/1984 | Dal Moro et al. | 71/DIG. 1 |
| 4,664,093 | 5/1987 | Bird et al. | 71/88 |
| 4,734,432 | 3/1988 | Szego et al. | 71/92 |

*Primary Examiner*—Richard L. Raymond
*Assistant Examiner*—Raymond Covington
*Attorney, Agent, or Firm*—Herbert Dubno; Jonathan Myers

[57] ABSTRACT

The invention relates to a plant-protective solution containing 2.5 to 40 % by weight of one or more water-insoluble plant-protective ingredient(s) 20 to 71.5 % by weight of dimethylformamide and/or dimethylsulfoxide and/or acetone as water-miscible solvent, 10 to 71.5 % by weight of furfurol and/or furfuryl alcohol as partially water-miscible solvent, 1 to 15 % by weight of commonly used additives such as anionic and/or nonionic surface active agents and macromolecules.

The invention also relates to the ready-for-use plant-protective suspension containing 0.2 to 10 % by weight of one or more water-insoluble plant-protective ingredient(s) with a particle size of 0.1 to 50 μm, 0 to 60 % by weight of a fertilizer, 0.2 to 10 % by weight of dimethylformamide and/or dimethylsulfoxide and/or acetone as water-miscible solvent, 0.2 to 10 % by weight of furfurol and/or furfuryl alcohol as partially water-miscible solvent, 0.05 to 2.5 by weight of a commonly used additive such as anionic and/or nonionic surface active agents macromolecules and water in an amount supplementing up to 100 % by weight.

10 Claims, No Drawings

PLANT-PROTECTIVE PESTICIDAL COMPOSITION

The invention relates to a plant-protective composition containing one or more water-insoluble plant-protective active ingredients dissolved in a water-miscible and/or partially water-miscible solvent in the presence of surface active agent(s) and/or protective colloid(s) and/or dispersing agent(s). On dilution with water of the composition according to the invention (on preparation of a spray fluid), the active ingredient spontaneously precipitates and a suspension with a suitable particle size is formed in the dose of the application. The suspension prepared in situ is also within the scope of the invention.

It is known that fluid compositions represent an important group of the plant-protective formulations. It is also known that, in the fluid formulations, the active ingredient is present in a solid state as a suspension or in a dissolved state.

When the active ingredient is chemically stable in water, the continuous phase of the suspension concentrates (FW) contains water as filling material. The physical and chemical properties of such compositions are regulated by suitable additives, usually by surface active agents, macromolecules, viscosity-influencing and anit-freeze agents.

In spite of the additives used, the stability of the suitably formulated plant-protective suspensions is limited; their most severe drawback consists in that the useful properties of the formulations can significantly be deteriorated under the effects of physical and chemical changes. Such changes are e.g. the crystallization or sedimentation of the solid phase of the suspension, formation of a hard, loamy layer or the like. Flocculation and aggregation of the suspension also occur frequently during the storage. Thess harmful phenomena result in an inhomogeneity of application of the active ingredient or a clogging while spraying. A part of the above disadvantages can be eliminated by using an organic liquid in a continuous phase.

However, severe difficulties arise from the formulation of suspensions containing non-aqueous media, when the liquid phase is water-immiscible. It is known that the active ingredient content of such formulations is strongly limited (a concentrate containing about 300 g/liter of active ingredient as a maximum can be prepared). A particular problem emerges from providing an appropriate rheology of the formulation and from the demand that the continuous phase of the FW containing a non-aqueous medium should be in a suitably emulsified state in the amount required for use.

Regarding such formulations, it is required that that a satisfactory suspension and emulsion stability should be provided in a spray fluid containing more than one heterogeneous phase.

Several problems should also be solved in the production of the emulsion concentrates (EC) today considered to be conventional formulations. It is known that there are a number of active ingredients which, when dissolved in a water-immiscible solvent and formulated with suitable emulsifiers, can be transformed to a stable emulsion after dilution with water. The most severe drawback of such formulations appears in the use of a solvent. The most frequently used solvents such as aromatic and aliphatic hydrocarbons or their mixtures are inflammable and explosive. An other problem arises since most of these solvents are phytotoxic within defined concentration range. Several companies producing solvents make efforts to develop solvents and solvent mixtures satisfying the severe criteria for the flash point and phytotoxicity. The basic costs of the products are significantly increased by the use of such materials.

In order to decrease the phytotoxicity as well as inflammability and explosivity, the concentrated emulsions (CE) were developed which are characterized in that a part of the water-immiscible solvent is replaced by water. A further property of these compositions consists in their capability to emulsify the water-immiscible solution of the active ingredients.

A novel trend of development can be considered to diminish the emulsified drop size below the C.1 $\mu$m range whereby thermodxnamically stable microemulsion systems can be established. A liquid active ingredient can be transformed to a microemulsion by using suitable additives and the disadvantages of using solvents may be avoided in this way.

In the simplest case, when the active ingredient is water-soluble and chemically stable in water, the aqueous solution containing appropriate additives is a suitable plant-protective formulation (L); however, considering the organic nature of the active ingredients, the number of such formulations (L) is low.

In a number of cases, such as when soil is disinfected by spraying, the criteria aimed to achieve a small size of particles or drops, respectively may means a drawback from the viewpoints of the biological efficiency, duration of the activity and utilization of the composition. When using suspension concentrates, a satisfying stability of the composition can be achieved with the adequate particle size of the solid phase, practically with an average particle size of 2 to 3 $\mu$m. However, this results in an extraordinarily strong adsorption of the active ingredient to the soil components or in the risk of a washing-out because of the very small particle size. It would be most favorable to keep the particle size of the solid phase within a defined range, practically between 5 and 50 $\mu$m whereby, however, the formulation would become unstable.

A similar problem arises from the low drop size of the spray fluid on the dilution of the emulsion concentrates.

The present invention is based on the recognition that a suspension with an adequate particle size can be formed and precipitated from a number of water-insoluble plant-protective active ingredients by dissolving them in a mixture of water-miscible and partially water-miscible solvents in the presence of suitable additives and diluting the solution thus obtained to the required application. The relation of the water-miscible solvent to the partially water-miscible solvent is 3.5–2.5: 1.5–0.5, preferably 3:1.

Thus, the present invention relates to a plant-protective solution containing 2.5 to 40% by weight of one or more water-insoluble plant-protective ingredient(s), 20 to 71.5% by weight of dimethylformamide and/or dimethylsulfoxide and/or acetone as water-miscible solvent, 10 to 71.5% by weight of furfurol and/or furfuryl alcohol as partially water-miscible solvent, 1 to 15% by weight of commonly used additives such as anionic and/or nonionic surface active agents and macromolecules (pre-composition).

The invention also relates to the ready-for-use plant-protective suspensions containing 0.2 to 10% by weight of one or more water-insoluble plant-protective ingredient(s) with a particle size of 0.1 to 50 $\mu$m, 0 to 60% by weight of a fertilizer, 0.2 to 10% by weight of dimethylformamide and/or dimethylsulfoxide and/or acetone as water-miscible solvent, 0.2 to 10% by weight of furfurol and/or furfuryl alcohol as partially water-miscible solvent, 0.05 to 2.5 by weight of a commonly used additive such as anionic and/or nonionic surface active agents macromolecules and water in an amount supplementing up to 100% by weight.

The plant-protective compositions according to the invention can be prepared in a simple way eliminating the disadvantages occurring during the preparation and storage of suspension concentrates. The compositions according to the invention are prepared by dissolving the required additive(s) in the solvent mixture used, then dissolving the plant-protective active ingredient at a temperature between 0° C. and 70° C., preferably at 50° C. under continuous stirring. After cooling the solution thus prepared to room temperature, a transparent solution is obtained. The agricultural user can prepare a spray fluid from the above composition by pouring an amount of the composition according to the invention to the water needed to spray or optionally to a solution or suspension containing another plant-protective active ingredient and/or a fertilizer to obtain a suspension which contains 0.1 to 5% by weight from the active ingredient of the pre-formulation.

On pouring the composition into water in the presence of suitably selected solvent mixture and additive, a suspension will be obtained with the desired particle size distribution.

The term "additive" as used herein means surface active agents and macromolecules. Anionic tensides are conveniently used as surface active agents. Particularly preferred tensides are alkylarylsulfonates (e.g. dodecylbenzenesulfonate salts) or alkylarylphosphates, aralkylsulfonates and -phosphates or their ethoxylated derivatives. In some cases it is advantageous to use nonionic tensides such as nonylor octylphenol polyglycol ethers or octylphenol polyether alcohols or ethoxylated fatty acids (e.g. ethoxylated oleic or cocoa acid).

Macromolecules (e.g. polyvinylpyrrolidone, polyvinyl alcohol, polyvinyl acetate and the like) may also be used as additives.

Surprisingly, we have found that those plant-protective agents which are crystalline at room temperature with a solubility lower than 1000 ppm in water and are well-soluble in the above define solvents or solvent mixtures, are useful to prepare the novel-type formulation according to the invention.

The following plant-protective agents may e.g. be used as active ingredients, in the composition according to the invention.

Carbamates

Bufencarb [a mixture of 3-(1-methylbutyl)phenyl methylcarbamate and 3-(1-ethylpropyl)phenylmethyl carbamate];
Carbaryl (1-naphthyl methylcarbamate);
Carbofuran (2,3-dihydro-2,2-dimethyl-7-benzofuranyl methylcarbamate);
Chloropropham (isopropyl 3-chlorophenyl carbamate);
Dioxacarb [2-(1,3-dioxolan-2-yl)phenyl methylcarbamate];
Promecarb (3-isopropyl-5-methylphenyl methylcarbamate);
Propoxur (2-isopropoxyphenyl methylcarbamate).

Esters of the Phosphoric and Thiophosphoric Acid

Bromophos [0-(4-bromo-2,5-dichlorophenyl)-0,0-dimethyl phosphorothioate];
Chlorpyrifos [0-(3,5,6-trichloro-2-pyridyl)-0,0-diethyl phosphorothioate];
Chlorpyrifos-methyl [0-(3,5,6-trichloro-2-pyridyl)-0,0-dimethyl phosphorothioate];
Dialifos (S-2-chloro-1-phthalimidoethyl-0,0-diethyl phosphorodithioate).

Urea Derivatives

Diflubenzurone [1-(4-chlorphenyl)-3-(2,6-difluorobenzoyl)urea];
Metabenzthiazurone (1-benzothiazol-2-yl-1,3-dimethylurea);
Metobromurone [3-(4-bromophenyl)-1-methoxy-1-methylurea];
Sidurone [1-(2-methylcyclohexyl)-3-phenylurea];
Thidiazurone [1-phenyl-2-(1,2,3-thiadiazol-5-yl)urea];

Nitro Derivatives

Dinitramine (N',N'-diethyl-2,6-dinitro-4-trifluoromethyl-m-phenylenediamine);
Dinoterb (2-tert-butyl-4,6-dinitrophenol);
Nitraline (4-methylsulfonyl-2,6-dinitro-N,N-dipropylaniline);
Trifluraline (2,6-dinitro-N,N-dipropyl-4-trifluoromethylaniline).

Acetamide Derivatives

Alachlor (2-chloro-2',6'-diethyl-N-methoxymethylacetanilide);
Cymoxanil [2-cyano-N-ethylaminocarbonyl-2-methoxyiminoacetamide).

Heterocyclic Compounds

Triazole Derivative

Diclobutrazole [(2RS,3RS)-1-(2,4-dichlorophenyl)-4,4-dimethyl-2-(1H-1,2,4-triazol-1-yl)pentan-3-ol].

Bicyclic Compound

Endosulfan (1,4,5,6,7,7-hexachloro-5-norbornene-2,3-dimethanol cyclic sulfite).

Oxazole Derivative

Hymexazole (5-methyl-3-isoxazol).

Imidazole Derivative

Iprodione [3-(3,5-dichlorophenyl)-N-(1-methylethyl)-2,4-dioxo-1-imidazolidinecarboxamide].

Piperazine Derivative

Triforine [1,4-piperazine-1,4-diyl-di[N-(2,2,2-trichloroethyl)formamide].

The particle size distribution of the active ingredient in the in situ prepared suspensions according to the invention was determined by using wet a sieving and supersound method.

The following results were obtained with the suspensions of various concentrations of the pre-composition described in Example 1.

| Particle size distribution in a suspension containing 0.2% carbofuran: | |
|---|---|
| Lower than 20 μm | 95% |
| Lower than 10 μm | 86% |

-continued

| | |
|---|---|
| Lower than 5 μ | 80% |
| Particle size distribution in a suspension containing 0.3% carbofuran | |
| Lower than 20 μ | 85% |
| Lower than 10 μm | 60% |
| Lower than 5 μ | 54% |
| Particle size distribution in a suspension containing 0.4% carbofuran | |
| Lower than 30 μm | 99% |
| Lower than 20 μm | 60% |
| Lower than 10 μm | 47% |
| Lower than 5 μm | 41% |
| Particle size distribution in a suspension containing 1% carbofuran: | |
| Lower than 45 μm | 83% |
| Lower than 30 μm | 81% |
| Lower than 20 μ | 28% |
| Lower than 10 μ | 14% |
| Lower than 5 μm | 9% |

The invention is illustrated in detail by the following non-limiting Examples.

Example 1

50 g of alkylaryl sulfonate (Atlox 4861B) are dissolved in the mixture of 187.5 g of furfurol and 562.5 g of dimethylformamide, then 200 g of carbofuran are dissolved in the above solution at 50° C. under continuous stirring. The solution is cooled to room temperature.

For the disinfection of soil, an aqueous suspension containing 0.2 to 1% by weight carbofuran is prepared from the above solution. On dilution with water, needle crystals of 5 to 50 μm in length and smaller than 5 μm in thickness are formed.

EXAMPLE 2

50 g of EL 1734 (Atlas ICI) are dissolved in the mixture of 187.5 g of furfurol and 562.5 g of dimethylformamide, then 200 g of carbofuran are dissolved therein at 50° C. under continuous stirring. The solution is cooled to room temperature.

For the disinfection of soil, an aqueous suspension containing 0.2 to 1% by weight carbofuran is prepared from the above solution. On dilution with water, prismatic crystals of 30 to 50 μm in length and 30 μm in thickness are formed.

EXAMPLE 3

25 g of alkylarylsulfonate (Atlox 4861B) and 25 g of EL 1734 (Atlas ICI) as surface active agents are dissolved in the mixture of 187.5 g of furfurol and 562.5 g of dimethylformamide, then 200 g of carbofuran are dissolved in the above solution at 50° C. under continuous stirring. The solution is cooled to room temperature.

For the disinfection of soil, an aqueous suspension containing 0.2 to 1% by weight carbofuran is prepared from the above solution. On dilution with water, crystals of 5 to 20 μm in length and smaller than 5 μm in thickness are formed.

EXAMPLE 4

50 g of phosphated calcium salt (Hoe S 2972) are dissolved in a mixture of 187.5 g of furfurol and 562.5 g dimethylformamide, then 200 g of carbofuran are dissolved at 50° C. in the above solution. The solution is cooled to room temperature.

For the disinfection of soil, an aqueous suspension containing 0.2 to 1% by weight carbofuran is prepared from the above solution. On dilution with water, needle crystals of 2 to 30 μm in size are formed (cloudy precipitation).

EXAMPLE 5

50 g of ethoxylated fatty acid (Genapol 0-050) are dissolved in the mixture of 187.5 g of furfurol and 562.5 g of dimethylformamide, then 200 g of carbofuran are dissolved at 50° C. in the above solution. The solution is cooled to room temperature.

For the disinfection of soil, an aqueous suspension containing 0.2 to 1% by weight carbofuran is prepared from the above solution. On dilution with water, prismatic crystals of 2 to 40 μm in size are formed.

EXAMPLE 6

50 g of Tensiofix 26100 (Tensia) as surface active agent are dissolved in a mixture of 187.5 g of furfurol and 562.5 g of dimethylformamide, then 200 g of carbofuran are dissolved at 50° C. in the above solution. The solution is cooled to room temperature.

For the disinfection of soil, an aqueous suspension containing 0.2 to 1% by weight carbofuran is prepared from the above solution. On dilution with water, crystals of 1 to 20 μm in size are formed (milky precipitation).

EXAMPLE 7

50 g of calcium dodecylbenzenesulfonate are dissolved in the mixture of 187.5 g of furfurol and 562.5 g of dimethylformamide, then 250 g of trifluraline are dissolved at 50° C. in the above solution. The solution is cooled to room temperature. The disperged phase of the aqueous dispersion with a concentration of 0.2 to 2% by weight prepared from the above solution has an average particle size of 1 to 30 μm.

EXAMPLE 8

50 g of ethoxylated fatty acid (Genapol 0-050) are dissolved in a mixture of 187.5 g of furfurol and 562.5 g of dimethylformamide, then 220 g of dioxacarb are dissolved at 50° C. in the above solution. The solution is cooled to room temperature.

For the disinfection of soil, an aqueous suspension containing 0.2 to 1% by weight dioxacarb is prepared from the above solution. On dilution with water prismatic crystals of 2 to 40 μm in size are formed.

EXAMPLE 9

50 g of ethoxylated fatty acid (Genapol 0-050) are dissolved in the mixture of 187.5 g of furfurol and 562.5 g of dimethylformamide, then 200 g of metabromurone are dissolved at 50° C. in the above solution. The solution is cooled to room temperature.

For the disinfection of soil, an aqueous suspension containing 0.2 to 1% by weight metabromurone is prepared from the above solution. On dilution with water, prismatic crystals of 2 to 70 μm in size are formed.

EXAMPLE 10

50 g of ethoxylated fatty acid (Genapol 0-050) are dissolved in the mixture of 187.5 g of furfurol and 562.5 g of dimethylformamide, then 200 g of endosulfan are dissolved at 50° C. in the above solution. The solution is cooled to room temperature.

For the disinfection of soil, an aqueous suspension containing 0.2 to 1% by weight endosulfan is prepared from the above solution. On dilution with water, prismatic crystals of 1 to 5 μm in size are formed.

EXAMPLE 11

50 g of ethoxylated fatty acid (Genapol 0–050) are dissolved in the mixture of 187.5 g of furfurol and 562.5 g of methylformamide, then 220 g of iprodione are dissolved at 50° C. in the above solution. The solution is cooled to room temperature.

For the disinfection of soil, an aqueous suspension containing 0.2 to 1% by weight iprodione is prepared from the above solution. On dilution with water, prismatic crystals of 2 to 9 μm in size are formed.

EXAMPLE 12

50 g of ethoxylated fatty acid (Genapol 0–050) are dissolved in the mixture of 187.5 g of furfurol and 562.5 g of dimethylformamide, then 200 g of chlorpyrifos are dissolved at 50° C. in the above solution. The solution is cooled to room temperature.

For the disinfection of soil, an aqueous suspension containing 0.2 to 1% by weight as calculated for chlorpyrifos is prepared from the above solution. On dilution with water, prismatic crystals of 3 to 15 μm in size are formed.

EXAMPLE 13

Study of the Biological Activity Against Pests

The liquid compositions were used in the form of a whole-surface treatment. The liquid soil-disinfecting compositions were applied in the form of a spray fluid, in an amount of 300 l/ha by using a Nowor 1005 type spraying machine and then worked in to a depth of 6 to 8 cm by a disc before the sowing of maize. The activity against the soil-inhabitant (terricol) pests was determined according to the MÉM-NAK methodological specifications. Experimental parcels of 500 m² in size were used. The examinations were carried out in four replications. Results are summarized in the following table:

| Composition | Dose 1 kg/ha | Carbofuran kg/ha | Activity % wireworm | Grub |
|---|---|---|---|---|
| Example 1 | 4.0 | 0.8 | 74 | 88 |
| Example 1 (a) | 6.0 | 1.2 | 82 | 100 |
| Chinufur 40 FW (b) | 4.0 | 1.6 | 87 | 100 |
| Chinufur 5 G | 15.0 | 0.75 | 81 | 88 |

(a) Chinufur 40 FW: an aqueous suspension formulation containing 40% of carbofuran (average particle size <5/μm)
(b) Chinufur 5 G: a granulate containing 5% by weight of carbofuran

EXAMPLE 14

Investigation of the Activity Against Soil-Inhabitant (Terricol) Pests (Agriotes)

Activity investigations were preformed against soil-inhabitant (terricol) pests by using the composition described in Example 1. The composition was applied in the usual way before sowing by using maize as test plant. These investigations were carried out in the Plant-Protective and Agrochemical Station (Komárom County) in four repetitions. The results are summarized in the following table:

| Composition | Dose kg/ha | Carbofuran kg/ha | Activity on wire worm % | Infection by frit fly % (Oscinalla fkut) | Damage of the maize silk % | Plants 20 × 10 m $\bar{x}$ pc./10 m | control % |
|---|---|---|---|---|---|---|---|
| Example 1 | 4.0 | 0.8 | 93.4 | 5.3 | 0.37 | 41.1 | 137.9 |
| Example 1 | 6.0 | 1.2 | 94.2 | 3.6 | 0.06 | 40.0 | 134.2 |
| Chinufur 40 FW | 4.0 | 1.6 | 98.0 | 3.3 | 0.12 | 40.4 | 135.6 |
| Cinufur 5 G | 30.0 | 1.5 | 91.7 | 3.8 | 0.31 | 39.9 | 133.8 |

All compositions were applied on the whole surface; the compositions 1 to 3 were sprayed onto the soil in an amount of 300 l/ha of spray fluid and worked in to a depth of 6 to 8 cm.

The activity again the wireworm was calculated by using the Schneider-Orelli formula $$E \text{ (Efficiency) } \% = \frac{T - c}{100 - c} \times 100$$

wherein
E means the activity (efficiency)
T means the percentage of the killed larvae during the treatment
c means the number of the dead control larvae.

EXAMPLE 15

Determination of the Activity of Liquid Soil-Disinfecting Compositions Plus Preplanting Herbicides The process described in Example 13 was followed, except that the liquid soil-disinfecting compositions were applied in the form of a combination containing a thiocarbamate active ingredient with a preplanting herbicide. The results are summarized in the following table:

| Composition | Dose kg/ha | Carbofuran kg/ha | Activity on wireworm % | Infection by frit fly % | Damage of the maize silk % | Plants 20 × 10 m | |
|---|---|---|---|---|---|---|---|
| | | | | | | pc/10 m | control % |
| Example 1 | 4.0 | 0.8 | 92.8 | 4.3 | 0.12 | 39.3 | 131.8 |
| + Alirox 80 EC | 7.0 | | | | | | |
| Example 1 | 6.0 | 1.2 | 96.0 | 4.12 | 0.12 | 40.6 | 136.2 |
| + Alirox 80 EC | 7.0 | | | | | | |
| Chinufur 40 FW | 4.0 | 1.6 | 95.7 | 3.9 | 0.06 | 39.8 | 133.6 |
| + Alirox 80 EC | 7.0 | | | | | | |
| Chinufur 5 G | 30.0 | 1.5 | 91.7 | 3.8 | 0.31 | 39.9 | 133.8 |

EXAMPLE 16

Determination of the Activity of a Combination With a Suspension Fertilizer

The composition described in Example 1 was applied in a combination with a suspension fertilizer (composition of the fertilizer: N:P:K=16:16:16% by weight) by using a Huniper 2000 type spraying equipment on C1/10/1981. The fertilizer suspension had a pH value of 7.4. The working-in was carried out to a depth of 6 to 10 cm by using a combinator before sowing. The evaluation was made at 24/04/1986. Autumn wheat was used as test plant with a seed-corn amount of 210 kg/ha. The experiment was carried out on a chernozem (black-earth) soil-type with a parcel size of 0.5 hectare in 2 repetitions. The activity of the compositions was evaluated against corn flies (Delia sp., Phorbia sp.) damaging the leaf sheath of the plants in the spring. The results are summarized in the following table:

| | Treatment | Dose 1 kg/ha | Carbofuran kg/ha | Damaged plants (8 × 1 m²) | Activity (Abbot) | Phytotoxicity |
|---|---|---|---|---|---|---|
| (1) | Example 1[x] | 5.0 | 1.0 | 8.4 | 80.42 | ∅ |
| (2) | Chinufur 40 FW[x] | 5.0 | 2.0 | 10.3 | 75.9 | ∅ |
| (3) | Example 1 + susp. fertilizer | 5.0 620 | 1.0 | 21.1 | 50.8 | ∅ |
| (4) | Chinufur 40 FW + susp. fertilizer | 5.0 620 | 2.0 | 22.7 | 47.1 | ∅ |
| (5) | Susp. fertilizer | 620 | — | 42.9 | — | ∅ |

[x]Treatments 1 and 2 were applied in an amount of 250 liters/ha in a spray fluid The composition described in Example 1 proved to be active against Delia and Phorbia spp. damaging the over-earth sprouts of the wheat after even 6 months following the treatment.

When applied in combination with a suspension fertilizer, its activity was less decreased than that of the Chinufur 40 FW liquid soil-disinfecting composition.

EXAMPLE 17

Use of furfurol/dimethylformamide in an 0.5:2.5 ratio 50 g of alkylarysulfonate are dissolved in a mixture containing 133.4 g of furfurol and 666.6 g of dimethylformamide (DMF) and 150 g of carbofuran are dissolved in the solution obtained while continuous stirring.

After cooling the solution to 20° C., an aqueous suspension of 0.2 to 1% by weight (as calculated for carbofuran) is prepared for soil disinfection. On dilution with water, needle crystals are formed which are 5 to 30 μm in length and smaller than 8 μm in thickness.

EXAMPLE 18

Use of furfurol/DMF in an 1.5:3.5 ratio 150 g of carbofuran are dissolved in a solution containing 50 g of alkylarylsulfonate in 240 g of furfurol and 560 g of DMF under continuous stirring.

After cooling the solution to 20° C., an aqueous suspension of 0.2 to 1% by weight (as calculated to carbofuran) is prepared for soil disinfection. On dilution with water, needle crystals are formed which are 5 to 20 μm in length and smaller than 7 μm in thickness.

We claim:

1. A plant-protective pesticidal solution containing 2.5 to 40% by weight of at least one water-insoluble plant-protective pesticidal ingredient, 20 to 71.5% by weight of dimethyl formamide and/or dimethyl sulfoxide, and/or acetone as water-miscible solvent, 10 to 71.5% by weight of furfural and/or furfuryl alcohol as partially water-miscible solvent, 1 to 15% by weight of anionic and/or nonionic surface active agents and macromolecules, wherein said plant-protective pesticidal solution upon addition to water being capable to form a suspension containing 0.2 to 10% by weight of said water-insoluble plant protective pesticidal ingredient having a particle size of 0.1 to 50 microns.

2. A plant protective pesticidal suspension containing 0.2 to 10% by weight of at least one water-insoluble plant-protective pesticidal ingredient with a particle size of 0.1 to 50 μm, 0 to 60% by weight of a fertilizer, 0.2 to 10% by weight of dimethylformamide and/or dimethylsulfoxide and/or acetone as water-miscible solvent, 0.2 to 10% by weight of furfurol and/or furfuryl alcohol as partially water-miscible solvent 0.05 to 2.5 by weight of anionic and/or nonionic surface active agents macromolecules and water in an amount supplementing up to 100% by weight.

3. A plant-protective pesticidal suspension as claimed in claim 2, which comprises as a carbamate-type coumpound at least one compound selected from the group consisting of a mixture of 3-(1-methylbutyl)phenyl methylcarbamate and
1-(1-ethylpropyl)phenyl methylcarbamate;
1-naphthyl methylcarbamate;
2,3-dihydro-2,2-dimethyl-7-benzofuranyl methylcarbamate;
isopropyl 3-chlorophenyl carbamate;
2-(1,3-dioxolan-2-yl)phenyl methylcarbamate;
3-isopropyl-5-methylphenyl methylcarbamate; and
2-isopropoxyphenyl methylcarbamate.

4. A plant prective pesticidal suspension as claimed in claim 2, which comprises as a phosphoric acid estertype compound at least one compound selected from the group consisting of
- 0-(4-bromo-2,5-dichlorophenyl)-0,0-dimethyl phosphorothioate;
- 0-(3,5,6-trichloro-2-pyridyl)-0,0-diethyl-phosphorothioate;
- 0-(3,5,6-trichloro-2-pyridyl)-0,0-dimethyl phosphorothioate; and
- S-2-chloro-1-phthalimidoethyl-0,0-diethyl phosphorodithioate.

5. A plant-protective pesticidal suspension as claim 2, which comprises as a urea-type compound at least one compound selected from the group consisting of
- 1-(4-chlorophenyl)-3-(2,6-difluorobenzoyl)urea;
- 1-benzothiazol-2-yl-1,3-dimethylurea;
- 3-(4-bromophenyl)-1-methoxy-1-methylurea;
- 1-(2-methylcyclohexyl)-3-phenylurea; and
- 1-phenyl-3-(1,2,3-thiadiazol-5-yl)urea.

6. A plant-protective pesticidal suspension as claimed in claim 2, which comprises as a nitro compound at least one compound selected from the group consisting of
- N',N'-diethyl-2,6-dinitro-4-trifluoromethyl-m-phenylenediamine;
- 2-tert.-butyl-4,6-dinitrophenol;
- 4-methylsulfonyl-2,6-dinitro-N,N-dipropylaniline; and
- 2,6-dinitro-N,N-dipropyl-4-trifluoromethylaniline.

7. A plant-protective pesticidal suspension as claimed in claim 2, which comprises as a acetamide compound at least one compound selected from the group consisting of
- 2-chloro-2',6'-diethyl-N-methoxymethylacetanilide; and
- 2-cyano-N-ethylaminocarbonyl-2-methoxyiminoacetamide.

8. A plant-protective pesticidal suspension as claimed in claim 2, which comprises as a heterocyclic compound at least one compound selected from the group consisting of
- (2RS,3RS)-1-(2,4-dichlorophenyl)-4,4-dimethyl-2-(1H-1,2,4-triazol-1-yl)pentan-3-ol;
- 1,4,5,6,7,7-hexachloro-5-norbornene-2,3-dimethanol cyclic sulfite;
- 5-methyl-3-isoxazolol;
- 3-(3,5-dichlorophenyl)-N-(1-methylethyl)-2,4-dioxo-1-imidazolidincarboxamide; and
- 1,4-piperazine-1,4-diyl-di[N-(2,2,2-trichloroethyl)formamide].

9. A plant-protective pesticidal suspension according to claim 2, wherein the relation of the water-miscible solvent to the partially water-miscible solvent is 3.5–2.5:5 1.5–0.5.

10. The plant-protective pesticidal suspension as claimed in claim 2 wherein the plant-protective ingredient is 2,3-dihydro-2,2-dimethyl-7-benzofuranyl-methylcarbamate, wherein the partially water-miscible solvent is furfurol, and wherein the water-miscible solvent is dimethylformamide.

* * * * *